US011959120B2

(12) United States Patent
Sun et al.

(10) Patent No.: US 11,959,120 B2
(45) **Date of Patent: *Apr. 16, 2024**

(54) METHOD OF MAKING LIPIDS WITH IMPROVED COLD FLOW PROPERTIES

(71) Applicant: MARA RENEWABLES CORPORATION, Dartmouth (CA)

(72) Inventors: Zhiyong Sun, Dartmouth (CA); Alan Sothern, Dartmouth (CA); Kevin Berryman, Dartmouth (CA); Mercia Valentine, Dartmouth (CA); Michael Milway, Dartmouth (CA); Laura Purdue, Dartmouth (CA); Roberto E. Armenta, Dartmouth (CA)

(73) Assignee: MARA Renewables Corporation, Dartmouth (CA)

( * ) Notice: Subject to any disclaimer, the term of this patent is extended or adjusted under 35 U.S.C. 154(b) by 227 days.

This patent is subject to a terminal disclaimer.

(21) Appl. No.: 17/083,045

(22) Filed: Oct. 28, 2020

(65) Prior Publication Data

US 2021/0040519 A1 Feb. 11, 2021

Related U.S. Application Data

(63) Continuation of application No. 15/178,890, filed on Jun. 10, 2016, now Pat. No. 10,851,395.

(51) Int. Cl.
*C12P 7/6427* (2022.01)
*C12P 7/6463* (2022.01)

(52) U.S. Cl.
CPC ........... *C12P 7/6427* (2013.01); *C12P 7/6463* (2013.01)

(58) Field of Classification Search
None
See application file for complete search history.

(56) References Cited

U.S. PATENT DOCUMENTS 4,341,038 A 7/1982 Bloch et al.
4,680,314 A 7/1987 Nonomura
4,952,511 A 8/1990 Radmer
5,070,018 A 12/1991 Peters et al.
5,104,803 A 4/1992 Delente
5,130,242 A 7/1992 Barclay
5,151,347 A 9/1992 Delente et al.
5,162,051 A 11/1992 Hoeksema
5,164,308 A 11/1992 Kyle
5,168,056 A 12/1992 Frost
5,171,680 A 12/1992 Mullenbach et al.
5,244,921 A 9/1993 Kyle et al.
5,272,073 A 12/1993 Frost et al.
5,324,658 A 6/1994 Cox et al.
5,340,594 A 8/1994 Barclay
5,340,742 A 8/1994 Barclay
5,374,657 A 12/1994 Kyle
5,376,540 A 12/1994 Kyle
5,397,591 A 3/1995 Kyle et al.
5,407,957 A 4/1995 Kyle et al.
5,466,434 A 11/1995 Kyle
5,487,987 A 1/1996 Frost et al.
5,492,938 A 2/1996 Kyle et al.
5,518,918 A 5/1996 Barclay
5,539,133 A 7/1996 Kohn et al.
5,547,699 A 8/1996 Tizuka et al.
5,550,156 A 8/1996 Kyle
5,567,732 A 10/1996 Kyle et al.
5,583,019 A 12/1996 Barclay
5,616,496 A 4/1997 Frost et al.
5,629,181 A 5/1997 Frost et al.
5,656,319 A 8/1997 Barclay
5,658,767 A 8/1997 Kyle
5,688,500 A 11/1997 Barclay
5,698,244 A 12/1997 Barclay
5,711,983 A 1/1998 Kyle et al.
5,882,703 A 3/1999 Barclay
5,908,622 A 6/1999 Barclay
5,985,348 A 11/1999 Barclay
6,027,900 A 2/2000 Allnutt et al.
6,054,147 A 4/2000 Barclay et al.
6,103,225 A 8/2000 Barclay
6,140,365 A 10/2000 Kiy et al.
6,140,486 A 10/2000 Facciotti et al.

(Continued)

FOREIGN PATENT DOCUMENTS

CN 101252844 A 8/2008
CN 101389749 3/2009

(Continued)

OTHER PUBLICATIONS

ECA Academy, What are the regulatory definitions for "Ambient", "Room Temperature" and "Cold Chain"? retrieved from URL: https://www.gmp-compliance.org/gmp-news/what-are-the-regulatory-definitions-for-ambient-room-temperature-and-cold-chain (Year: 2017).*
CA3,027,005 , "Office Action", dated Sep. 15, 2022, 4 pages.
EP22177911.9 , "Extended European Search Report", dated Sep. 20, 2022, 8 pages.
Jakobsen et al., "Accumulation of Docosahexaenoic Acid-Rich Lipid in *Thraustochytrid aurantiochytrium* Sp. Strain T66: Effects of N and p Starvation and O2 Limitation", Applied Microbiology and Biotechnology, vol. 80, No. 2, Jun. 17, 2008, pp. 297-306.
Lowrey et al., "Nutrient Recycling of Lipid-extracted Waste in the Production of an Oleaginous Thraustochytrid", Applied Microbiology and Biotechnology, Springer, DE, vol. 100, No. 10, Mar. 22, 2016, pp. 4711-4721.

(Continued)

*Primary Examiner* — Allison M Fox
(74) *Attorney, Agent, or Firm* — Kilpatrick Townsend & Stockton LLP

(57) ABSTRACT

Provided herein are methods of producing oils with reduced saturated fatty acids. The methods include culturing oil-producing microorganisms in a fermentation medium in the presence of one or more antifoaming agents under a controlled carbon consumption rate, wherein the culturing produces oils comprising fatty acids and wherein less than 35% of the fatty acids in the oil are saturated fatty acids.

23 Claims, 4 Drawing Sheets

(56) References Cited

U.S. PATENT DOCUMENTS

| | | | |
|---|---|---|---|
| 6,166,230 | A | 12/2000 | Bijl et al. |
| 6,166,231 | A | 12/2000 | Hoeksema |
| 6,177,108 | B1 | 1/2001 | Barclay |
| 6,180,376 | B1 | 1/2001 | Liddell |
| 6,255,505 | B1 | 7/2001 | Bijl et al. |
| 6,350,890 | B1 | 2/2002 | Kiy et al. |
| 6,372,460 | B1 | 4/2002 | Gladue et al. |
| 6,395,778 | B1 | 5/2002 | Luthria |
| 6,399,803 | B1 | 6/2002 | Corley et al. |
| 6,410,281 | B1 | 6/2002 | Barclay |
| 6,410,282 | B1 | 6/2002 | Kumar et al. |
| 6,441,208 | B2 | 8/2002 | Bijl et al. |
| 6,451,567 | B1 | 9/2002 | Barclay |
| 6,461,839 | B2 | 10/2002 | Yokochi et al. |
| 6,509,178 | B1 | 1/2003 | Tanaka et al. |
| 6,541,049 | B2 | 4/2003 | Barclay |
| 6,566,123 | B1 | 5/2003 | Barclay |
| 6,568,351 | B1 | 5/2003 | Barclay et al. |
| 6,582,941 | B1 | 6/2003 | Yokochi et al. |
| 6,596,766 | B1 | 7/2003 | Igarashi et al. |
| 6,607,900 | B2 | 8/2003 | Bailey et al. |
| 6,727,373 | B2 | 4/2004 | Bijl et al. |
| 6,749,849 | B2 | 6/2004 | Barclay |
| 6,750,048 | B2 | 6/2004 | Ruecker et al. |
| 6,783,951 | B2 | 8/2004 | Long, II |
| 6,812,009 | B2 | 11/2004 | Gladue et al. |
| 6,977,167 | B2 | 12/2005 | Barclay |
| 7,001,772 | B2 | 2/2006 | Roessler et al. |
| 7,005,280 | B2 | 2/2006 | Barclay |
| 7,011,962 | B2 | 3/2006 | Barclay |
| 7,022,512 | B2 | 4/2006 | Barclay |
| 7,033,584 | B2 | 4/2006 | Barclay |
| 7,063,855 | B2 | 6/2006 | Hjaltason et al. |
| 7,067,145 | B2 | 6/2006 | Place et al. |
| 7,247,461 | B2 | 7/2007 | Metz et al. |
| 7,259,006 | B2 | 8/2007 | Komazawa et al. |
| 7,351,558 | B2 | 4/2008 | Ruecker et al. |
| 7,374,908 | B2 | 5/2008 | Yamaoka |
| 7,381,558 | B2 | 6/2008 | Barclay |
| 7,419,596 | B2 | 9/2008 | Dueppen et al. |
| 7,514,244 | B2 | 4/2009 | Tanaka et al. |
| 7,923,226 | B2 | 4/2011 | Frost |
| 8,163,515 | B2 | 4/2012 | Burja et al. |
| 8,168,225 | B2 | 5/2012 | Casana et al. |
| 8,202,713 | B2 | 6/2012 | Wen et al. |
| 8,541,210 | B2 | 9/2013 | Wen et al. |
| 9,023,616 | B2 | 5/2015 | Radianingtyas et al. |
| 10,385,370 | B2 | 8/2019 | Sun et al. |
| 2001/0025114 | A1 | 9/2001 | Bijl et al. |
| 2003/0060509 | A1 | 3/2003 | Elswyk |
| 2003/0143659 | A1 | 7/2003 | Bijl et al. |
| 2003/0161864 | A1 | 8/2003 | Tanaka et al. |
| 2003/0180898 | A1 | 9/2003 | Bailey et al. |
| 2004/0067574 | A1 | 4/2004 | Bijl et al. |
| 2004/0092590 | A1 | 5/2004 | Arterburn et al. |
| 2004/0161831 | A1 | 8/2004 | Komazawa et al. |
| 2005/0027004 | A1 | 2/2005 | Kyle et al. |
| 2005/0129831 | A1 | 6/2005 | Fabritius |
| 2005/0170479 | A1 | 8/2005 | Weaver et al. |
| 2006/0094089 | A1 | 5/2006 | Barclay |
| 2007/0003686 | A1 | 1/2007 | Fichtali et al. |
| 2007/0104856 | A1 | 5/2007 | Standal et al. |
| 2007/0112071 | A1 | 5/2007 | Bryhn et al. |
| 2007/0184090 | A1 | 8/2007 | Van Waterschoot et al. |
| 2007/0243307 | A1 | 10/2007 | Abril et al. |
| 2007/0248586 | A1 | 10/2007 | Arterburn et al. |
| 2008/0155888 | A1 | 7/2008 | Vick et al. |
| 2008/0220515 | A1 | 9/2008 | McCall |
| 2009/0029445 | A1 | 1/2009 | Eckelberry et al. |
| 2009/0064567 | A1 | 3/2009 | Lippmeier et al. |
| 2009/0077863 | A1 | 3/2009 | Oyler |
| 2009/0081748 | A1 | 3/2009 | Oyler |
| 2009/0117194 | A1 | 5/2009 | Burja et al. |
| 2010/0099901 | A1 | 4/2010 | Hayashi et al. |
| 2010/0291630 | A1 | 11/2010 | Cox et al. |
| 2012/0244584 | A1 | 9/2012 | Zhang et al. |
| 2013/0129775 | A1 | 5/2013 | Shinde et al. |
| 2013/0217084 | A1 | 8/2013 | Wen |
| 2014/0141495 | A1 | 5/2014 | Varadaraj |
| 2016/0309748 | A1 | 10/2016 | Apt et al. |
| 2018/0208954 | A1* | 7/2018 | Sun ...................... C12P 7/6427 |

FOREIGN PATENT DOCUMENTS

| | | | |
|---|---|---|---|
| CN | 101575584 | | 11/2009 |
| CN | 101575584 | | 12/2010 |
| CN | 102037129 | A | 4/2011 |
| CN | 103805514 | | 5/2014 |
| CN | 104313068 | | 1/2015 |
| CN | 105154481 | A | 12/2015 |
| CN | 105154483 | | 12/2015 |
| EP | 0707487 | A1 | 4/1996 |
| EP | 0831805 | A1 | 4/1998 |
| EP | 1506996 | A2 | 2/2005 |
| EP | 2337857 | A1 | 6/2011 |
| EP | 2391361 | A1 | 12/2011 |
| EP | 2405895 | A1 | 1/2012 |
| EP | 2960325 | | 12/2015 |
| EP | 2960325 | | 9/2017 |
| EP | 3385359 | | 10/2018 |
| GB | 2379166 | A | 3/2003 |
| JP | H08163990 | A | 6/1996 |
| JP | H0975000 | A | 3/1997 |
| JP | H1072590 | A | 3/1998 |
| JP | 2000060587 | A | 2/2000 |
| WO | 8703899 | | 7/1987 |
| WO | 8900606 | | 1/1989 |
| WO | 9213086 | | 8/1992 |
| WO | 9428891 | A1 | 12/1994 |
| WO | 9737032 | | 10/1997 |
| WO | 0005395 | | 2/2000 |
| WO | 0054575 | | 9/2000 |
| WO | 0149282 | A2 | 7/2001 |
| WO | 0210322 | | 2/2002 |
| WO | 02092540 | | 11/2002 |
| WO | 2005083093 | A2 | 9/2005 |
| WO | 2007068997 | | 6/2007 |
| WO | 2007069078 | | 6/2007 |
| WO | 2007074479 | | 7/2007 |
| WO | 2008090989 | | 7/2008 |
| WO | 2008129358 | | 10/2008 |
| WO | 2009029793 | A1 | 3/2009 |
| WO | 2009034124 | | 3/2009 |
| WO | 2009118150 | A1 | 10/2009 |
| WO | 2015177641 | A2 | 11/2015 |
| WO | 2015179844 | | 11/2015 |
| WO | 2016059540 | | 4/2016 |
| WO | 2017212322 | | 12/2017 |

OTHER PUBLICATIONS

Application No. CN201680085912.0 , Office Action, dated Mar. 2, 2021, 8 pages.

Application No. CA3,027,005 , Office Action, dated Dec. 11, 2020, 5 pages.

Thraustochytriaceae Family Data Sheet, Jun. 7, 2007, 2 pages.

"Breakthrough Process to Extract Oil from Algae", Available Online at: http://www.miningtopnews.com/originoil-announces-breakthrough-process-to-extract-oil-from -.htm., Apr. 20, 2009, pp. 1-4.

"Natural Trans Fats Have Health Benefits, New Study Shows", Science Daily, University of Alberta, available online at, www.sciencedaily.com/releases/2008/04/080402152140.html, Apr. 5, 2008, 3 pages.

"Oil from Algae", Oilgae Glossary, Available Online at: http://www.oilgae.com/algae/oil/extract/extract.html, Jun. 4, 2009, pp. 1-8.

"Omega-3 News", Ocean Nutrition Canada Ltd., 2011, 3 pages.

U.S. Appl. No. 15/178,890 , Final Office Action, dated Dec. 13, 2019, 16 pages.

U.S. Appl. No. 15/178,890 , Final Office Action, dated Sep. 4, 2018, 18 pages.

U.S. Appl. No. 15/178,890 , Non-Final Office Action, dated Jun. 24, 2019, 18 pages.

(56) References Cited

OTHER PUBLICATIONS

U.S. Appl. No. 15/178,890 , Non-Final Office Action, dated Feb. 22, 2018, 23 pages.
U.S. Appl. No. 15/178,890 , Non-Final Office Action, dated Jul. 17, 2020, 8 pages.
U.S. Appl. No. 15/178,890 , "Restriction Requirement", dated Sep. 27, 2017, 7 pages.
U.S. Appl. No. 15/926,680 , Final Office Action, dated Feb. 5, 2019, 23 pages.
U.S. Appl. No. 15/926,680 , Non-Final Office Action, dated Jul. 26, 2018, 15 pages.
AU2016410102 , "First Examination Report", dated Aug. 12, 2019, 4 pages.
Bajpai et al., "Optimization of Production of Docosahexaenoic Acid (DHA) byThraustochytrium Aureum ATCC 34304", Journal of the American Oil Chemists Society, vol. 68, No. 7, Jul. 1991, pp. 509-514.
Bajpai et al., "Production of Docosahexaenoic Acid by Thraustochytrium Aureum", Applied Microbiology and Biotechnology, vol. 35, No. 6, Sep. 1991, pp. 706-710.
Baldwin , "Application for the Approval of DHA-Rich Oil", Omega Tech GmbH, Version No. Draft, 1997, 104 pages.
Barclay et al., "Heterotrophic Production of Long Chain Omega-3 Fatty Acids Utilizing Algae and Algae-Like Microorganisms", Journal of Applied Phycology, vol. 6, Issue 2, Apr. 1994, pp. 123-129.
Bateman et al., "Method for Extraction and Separation by Solid Phase Extraction of Neutral Lipid, Free Fatty Acids, and Polar Lipid from Mixed Microbial Cultures", Journal of Agricultural and Food Chemistry, Jan. 20, 1997, pp. 132-134.
Bernstein et al., "Purified Palmitoleic Acid for the Reduction of High-Sensitivity C-Reactive Pprotein and Serum Lipids: A Double-Blinded, Randomized, Placebo Controlled Study", Journal of Clinical Lipidology, vol. 8, No. 6, 2014, pp. 612-617.
Bligh et al., "A Rapid Method of Total Lipid Extraction and Purification", Canadian Journal of Biochemistry and Physiology, vol. 37 No. 8, Aug. 1959, pp. 911-917.
Bowles et al., "Long-Chain N-3 Polyunsaturated Fatty Acid Production by Members of the Marine Protistan Group the Thraustochytrids: Screening of Isolates and Optimisation of Docosahexaenoic Acid Production", Journal of Biotechnology, vol. 70, Nos. 1-3, Apr. 1999, pp. 193-202.
Application No. BR1120180743151 , Office Action, dated Jan. 28, 2020, 7 pages.
Burja et al., "Evaluation of Fatty Acid Extraction Methods for Thraustochytrium sp. ONC-T18", Journal of Agricultural and Food Chemistry, vol. 55, No. 12, May 12, 2007, pp. 4795-4801.
Burja et al., "Isolation and Characterization of Polyunsaturated Fatty Acid producing Thraustochytrium Species: Screening of Strains and Optimization of Omega-3 Production", Applied Microbiology and Biotechnology, vol. 72, No. 6, Apr. 20, 2006, pp. 1161-1169.
Application No. CA3,027,005, Office Action, dated Dec. 5, 2019, 4 pages.
Application No. EP16904537.4 , Extended European Search Report, dated Jan. 8, 2020, 9 pages.
Application No. EP16904537.4 , Office Action, dated Mar. 12, 2019, 3 pages.
Field et al., "Human Health Benefits of Vaccenic Acid", Applied Physiology Nutrition and Metabolism, vol. 34, No. 5, Oct. 2009, pp. 979-991.
Fu et al., "Study on Production of EPA and DHA in Microbe Fermentation", Grain Processing, No. 1, 2004, pp. 48-51.
Grima et al., "Recovery of Microalgal Biomass and Metabolites: Process Options and Economics", Biotechnology Advances, vol. 20, Nos. 7-8, Jan. 2003, pp. 491-515.
Hauvermale et al., "Fatty Acid Production in *Schizochytrium* ; sp.: Involvement of a Polyunsaturated Fatty Acid Synthase and a Type 1 Fatty Acid Synthase", LIPIDS, vol. 41, No. 8, 2006, pp. 739-747.
Howlett et al., "DHA-Rich Algal Oil From *Schizochytrium* Sp.", ONC-T18, Ocean Nutrition Canada Limited, Retrieved from the Internet: https://acnfp.food.gov.uk/sites/default/files/mnt/drupal_data/sources/files/multimedia/pdfs/dhaoilont.pdf, 2011, pp. 1-74.
Iida et al., "Improvement of Docosahexaenoic Acid Production in a Culture of Thraustochytrium Aureum by Medium Optimization", Journal of Fermentation and Bioengineering, vol. 81, Issue 1, 1996, pp. 76-78.
IN201817048962 , "First Examination Report", dated Aug. 27, 2020, 6 pages.
Kaulmann et al., "Biosynthesis of Polyunsaturated Fatty Acids by Polyketide Synthases", Angewandte Chemie International Edition, vol. 41, Issue 11, Jun. 3, 2002, pp. 1866-1869.
Lewis et al., "Evaluation of Extraction Methods for Recovery of Fatty Acids from Lipid-Producing Microheterotrophs", Journal of Microbiological Methods, vol. 43, Issue 2, Dec. 15, 2000, pp. 107-116.
Li et al., "Production of Docosahexaenoic Acid by Thraustochytrium Roseum", Journal of Industrial Microbiology, vol. 13, Issue 4, Aug. 1994, pp. 238-241.
Liu et al., "Study on Production of EPA and DHA in Microbe Fermentation", Food Science and Technology, No. 6, 2004, pp. 13-16.
Marine Biopharmacy , "Marine Biopharmacy Fermentation Engineering", Beijing Chemical Industry Press, 2002, pp. 96-101.
Meng et al., "Biodiesel Production From Oleaginous Microorganisms", Renewable Energy, vol. 34, No. 1, Jan. 2009, pp. 1-5.
Metz et al., "Production of Polyunsaturated Fatty Acids by Polyketide Synthases in both Prokaryotes and Eukaryotes", Science, vol. 293, Issue 5528, Jul. 2001, pp. 290-293.
Nagano et al., "Optimization of Culture Conditions for Growth of Docosahexaenoic Acid Production by a Marine Thraustochytrid, Aurantiochytrium Limacinum Mh0186", Journal of Oleo Science, vol. 58, Issue 12, 2009, pp. 623-628.
Nakahara et al., "Production of Docosahexaenoic and Docosapentaenoic Acids by *Schizochytrium* sp. Isolated from Yap Islands", Journal of the American Oil Chemists Society, vol. 73, No. 11, Nov. 1996,, pp. 1421-1426.
Ohara et al., "Two Fatty Acid Elongases Possessing C18-Δ6/C18-Δ9/C20-Δ5 or C16-Δ9 Elongase Activity in *Thraustochytrium* sp. ATCC 26185", Marine Biotechnology, vol. 15, Issue 4, Aug. 2013, pp. 476-486.
Application No. PCT/IB2016/053586 , International Preliminary Report on Patentability, dated Dec. 20, 2018, 8 pages.
Application No. PCT/IB2016/053586 , International Search Report and Written Opinion, dated Feb. 20, 2017, 11 pages.
Pinkart et al., "Rapid Separation of Microbial Lipids using Solid Phase Extraction Columns", Journal of Microbiological Methods, vol. 34, Issue 1, Sep. 1, 1998, pp. 9-15.
Ratledge et al., "Single Cell Oils—A Coming of Age", Lipid Technology, vol. 16, Feb. 2004, pp. 34-39.
Sijtsma et al., "Recent Advances in Fatty Acid Synthesis in Oleaginous Yeasts and Microalgae", Recent Research Developments in Microbiology, vol. 2, Jan. 1998, pp. 219-232.
Singh et al., "Docosahexaenoic Acid (DHA) Production by *Thraustochytrium* Sp. ATCC 20892", World Journal of Microbiology and Biotechnology, vol. 12, No. 1, Jan. 1996, pp. 76-81.
Song et al., "Effective Phase Separation of Biomass Pyrolysis Oils by Adding Aqueous Salt Solutions", Energy and Fuels, vol. 23, 2009, pp. 3307-3312.
Wardencki et al., "Trends in Solventless Sample Preparation Techniques for Environmental Analysis", Journal of Biochemical and Biophysical Methods, vol. 70, Issue 2, 2007, pp. 275-288.
Yamaoka et al., "Growth Characterization and Resources of Thraustochytrium CHN-1 Isolated from the Seto Inland Sea", Bulletin of the Society of Sea Water Science, Japan, vol. 59, No. 1, 2005, pp. 23-31.
Yang et al., "Chronic Administration of Palmitoleic Acid Reduces Insulin Resistance and Hepatic Lipid Accumulation in KK-Ay Mice with Genetic Type 2 Diabetes", Lipids in Health and Disease, vol. 10, No. 120, Jul. 21, 2011, pp. 1-8.
Yokochi et al., "Optimization of Docosahexaenoic Acid Productions by Schizochytrium Limacinum SR21", Applied Microbiology and Biotechnology, vol. 49, Issue 1, Jan. 1998, pp. 72-76.

(56) References Cited

OTHER PUBLICATIONS

Application No. CN201680085912.0 , Office Action, dated Oct. 15, 2021, 6 pages.
Application No. EP16 904 537.4 , Office Action, dated Aug. 30, 2021, 9 pages.
Bin et al., "The Tribological and Biodegradable Characteristic of the Light Sulfurized Castor Oil as Base Oil", Lubrication Engineering, No. 4, Apr. 15, 2006, 3 pages.
Application No. CN201680085912.0 , Office Action, dated Jan. 17, 2022, 4 pages.
Yajun et al., "Determination and Evaluation of Coconut Oil as Base Oil for Industrial Lubricants", Scientific and Technological Knowledge, vol. 16, No. 3, May 12, 2008, 4 pages.
Application No. CA3,027,005 , Office Action, dated Nov. 8, 2021, 3 pages.
AU2020203821 , "First Examination Report", dated Aug. 6, 2021, 3 pages.
Application No. CN201680085912.0 , Office Action, dated Aug. 17, 2021, 3 pages.
Application No. EP16904537.4 , Office Action, dated Feb. 11, 2022, 7 pages.
Ludevese-Pascual et al., "Biomass Production, Proximate Composition and Fatty Acid Profile of the Local Marine Thraustochytrid Isolate, *Schizochytrium* Sp. Ley7 Using Low-Cost Substrates at Optimum Culture Conditions", Aquaculture Research, vol. 47, 2016, pp. 318-328.
Shibahara et al., "cis-Vaccenic Acid in Mango Pulp Lipids", Lipids, vol. 21, No. 6, 1986, pp. 388-394.
Bin, "Study on Tribological Properties and Reactivity of Novel Modified Vegetable Oil and Environmentally Friendly Lubricants", Shanghai University Press,, Dec. 31, 2003, 2 pages.
BR1120180743151, "Office Action", dated Oct. 10, 2023, 18 pages.
CN202210140036.4, "Office Action", dated Sep. 14, 2023, 9 pages.
AU2022201863, "First Examination Report", dated May 31, 2023, 4 pages.

* cited by examiner

METHOD OF MAKING LIPIDS WITH IMPROVED COLD FLOW PROPERTIES

CROSS-REFERENCE TO RELATED APPLICATION

This application is a continuation of U.S. application Ser. No. 15/178,890, filed Jun. 10, 2016, which is currently pending and incorporated by reference herein in its entirety.

BACKGROUND

Microbial oils have attracted significant consumer and commercial attention as a sustainable, environmentally friendly and vegetarian source of nutritional lipids to provide essential fatty acids such as DHA, DPA and EPA to human and animals. Current academic and industrial production of microbial oil depends on production strain discovery and/or genetic modification to make microbial oil with desired compositions and/or physical properties. However, it is challenging to customize the fatty acid profile of the oils with desired physical and nutritional properties. Oil customization is particularly challenging to achieve through fermentation conditions only, without genetic modification of the microorganisms. Microbial oils are typically waxy at ambient temperature conditions. The solidified microbial oils require heating to melt it in order to facilitate handling. Handling oil at high temperatures, however, can be difficult or unfeasible for existing edible oil refining facilities. Furthermore, lipid stability and quality may be affected negatively due to prolonged exposure to elevated temperatures. Such heated oil likely requires further processing to maintain lipid quality, such as addition of antioxidants and application of strict blanketing with nitrogen. All of these additional processing requirements may affect the final lipid quality of the oil and increase processing costs.

SUMMARY

Provided herein are methods of producing oils with reduced saturated fatty acids. The methods include culturing oil-producing microorganisms in a fermentation medium in the presence of one or more antifoaming agents under a controlled carbon consumption rate, wherein the culturing produces oils comprising fatty acids and wherein less than 35% of the fatty acids in the oils are saturated fatty acids.

DETAILED DESCRIPTION

Figure 1:
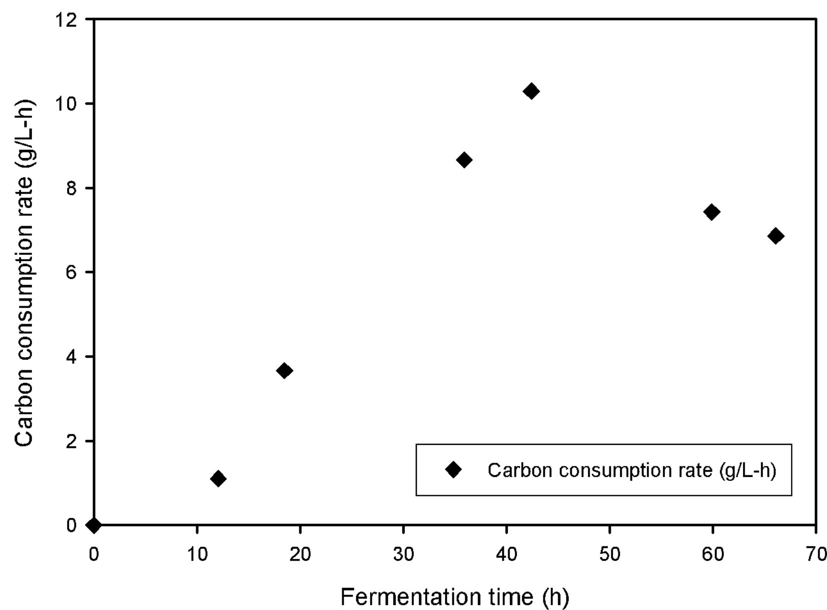
FIG. 1 is a graph showing unrestricted carbon consumption rate during a low-DHA fermentation.

Described herein is a microbial fermentation process that produces oils rich in omega-3 fatty acids (i.e., C22:6 (n-3) docosahexaenoic acid, DHA), omega-6 fatty acids (i.e., C22:5 (n-6) docosapentaenoic acid, DPA), and omega-7 fatty acids (i.e., C16:1 (n-7) palmitoleic acid and C18:1 (n-7) vaccenic acid) and low in saturated fatty acids (i.e., C16:0 palmitic acid and C14:0 myristic acid). Such fatty acid profiles not only satisfy the need for the oils to be classified and used as DHA-rich or omega-3 rich nutritional oils, the oils also have improved nutritional composition and value due to the increased content of omega-7 fatty acids. The oils also have improved cold flow properties due to the reduced content of saturated fatty acids in the oil. Compared to oils produced using previous fermentation methods, the improved nutritional value of the oils is shown by an increase in omega-3 fatty acid content (i.e., DHA) and an increase in omega-7 fatty acid content (i.e., palmitoleic acid and vaccenic acid) (FIG. 1). The improved cold flow properties of the oils include improved melting, cloud and pour points. For example, as described herein, the oils produced by the provided methods include a reduced pour point of as low as −9° C., a much lower pour point range than a typical lipids produced by previous fermentation process conditions, which varied between 18° C. and 21° C. (Table 1).

By applying the process conditions described herein, including controlled antifoam addition as well as controlled carbon consumption rate, the microorganisms were able to produce oils with significantly increased amounts of polyunsaturated fatty acids (PUFA) and monounsaturated fatty acids (MUFA) and reduced saturated fatty acids (SFA) as compared to oils produced by previous fermentation methods. Due to these changes in fatty acid composition, the oils had a reduced melting point, cloud point, and pour point. Consequently, the oils exhibited significantly improved cold flow properties. Furthermore, the oils contain an improved nutritional value due to the increase in PUFA (DHA and DPA) and increase in MUFA (omega-7 fatty acids).

As used herein, the term melting point refers to the temperature at which the oil becomes completely clear. As used herein, the term cloud point refers to the temperature of the oil at which the oil begins to crystalize. As used herein, the pour point is an index of the lowest temperature at which movement of the test specimen (e.g., oil) is observed under prescribed conditions of test. These temperatures can be determined by known methods including those established by the American Oil Chemistry Society (AOCS) and American Society of Testing and Materials (ASTM), which establishes specifications for determining the melting, cloud and pour points of fluids such as lipids and oils. For example, melting point can be determined using AOCS Official Method Cc 1-25, cloud point can be determined using AOCS Official Method Cc 6-25 and pour point can be determined using ASTM Official Method D97.

Provided herein is a method of producing oils with reduced saturated fatty acids. The method includes culturing oil-producing microorganisms in a fermentation medium in the presence of one or more antifoaming agents under a controlled carbon consumption rate, wherein the culturing produces oils comprising fatty acids and wherein less than 35% of the fatty acids in the oils are saturated fatty acids.

Suitable antifoaming agents include, but are not limited to, mineral oil based antifoaming agents, vegetable oil based antifoaming agents, silicon based antifoaming agents, oil/water emulsion based antifoaming agents, polyethylene glycol (PEG) based antifoaming agents, and polypropylene glycol based antifoaming agents. Suitable vegetable oil based antifoaming agents include, but are not limited to, soybean oil and rapeseed oil. Suitable silicon based antifoaming agents include, but are not limited to, poly dimethyl siloxane.

During culturing, the antifoaming agent or agents can be added to the fermentation medium continuously or intermittently. Optionally, the one or more antifoaming agents are continuously added to the fermentation medium throughout the culturing. Optionally, the one or more antifoaming agents are added intermittently to the fermentation medium throughout the culturing. Optionally, the antifoaming agents are added every 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or any amount of time between 1 and 30 minutes inclusive, throughout the culturing. Optionally, the antifoaming agents are added every 1, 2, 3, 4, 5, 6, 7, 8, 9, 10, 15, 20, 25, 30, 35, 40, 45, 50, 55, or 60 seconds or any amount of time between 1 and 60 seconds inclusive, throughout the culturing. Optionally, the one or more antifoaming agents are added to the fermentation medium at a rate of 0.0075 to 0.05 g/L per hour.

As described herein, the method includes culturing oil-producing microorganisms in fermentation medium in the presence of one or more antifoaming agents under a controlled carbon consumption rate. Optionally, the carbon consumption rate is controlled to be between 1.5 and 4.5 g/L per hour. Optionally, the carbon consumption rate is controlled to be between 0.01 to 0.15 g of carbon per g of biomass per hour. The carbon consumption rate can be controlled by a variety of methods. Optionally, the carbon consumption rate is controlled by aeration, agitation, vessel backpressure or a combination thereof. Optionally, the carbon consumption rate is controlled by continuous addition of a (one or more) carbon source(s) throughout the culturing.

The oils produced by the provided methods have improved cold flow properties, e.g., they have improved melting, cloud, and pour point temperatures. Thus, the oils made by the provided methods can have a melting point of from 20 to 33° C. or any temperature between 20 and 33° C. inclusive. Thus, the oils can have a melting point temperature of 20, 21, 22, 23, 24, 25, 26, 27, 28, 29, 30, 31, 32, or 33° C. or any fraction thereof. Optionally, the oils made by the provided methods have a cloud point of from 5 to 20° C. or any temperature between 5 and 20° C. inclusive. Thus, the oils can have a cloud point temperature of 5, 6, 7, 8, 9, 10, 11, 12, 13, 14, 15, 16, 17, 18, 19, or 20° C. or any fraction thereof. Optionally, the oils made by the provided methods have a pour point of −10 to 15° C. or any temperature between −10 and 15° C. inclusive. Thus, the oils can have a pour point temperature of −10, −9, −8, −7, −6, −5, −4, −3, −2, −1, 0, 1, 2, 3, 4, 5, 6, 7, 8, 9, 10, 11, 12, 13, 14, or 15° C. or any fractional temperature between.

As described herein, culturing the oil-producing microorganisms in the fermentation medium in the presence of one or more antifoaming agents under a controlled carbon consumption rate produces oils having fatty acids wherein less than 35% of the fatty acid in the oils are saturated fatty acids. Optionally, less than 20% of the fatty acids in the oils are saturated fatty acids. Optionally, less than 25% of the fatty acids in the oils are saturated fatty acids. Optionally, less than 30% of the fatty acids in the oils are saturated fatty acids. Thus, optionally, less than 15, 16, 17, 18, 19, 20, 21, 22, 23, 24, 25, 26, 27, 28, 29, 30, 31, 32, 33, or 35% of the fatty acids in the oils are saturated fatty acids. The percent saturated fatty acids is expressed throughout as a percent of the total fatty acids in the oil. Optionally, 30% to 35% of the fatty acids in the oils are saturated fatty acids and the oils are flowable at a temperature between 9 and 15° C. Optionally, 25% to 30% of the fatty acids in the oils are saturated fatty acids and the oils are flowable at a temperature between −9° C. and 9° C. Optionally, less than 25% of the fatty acids in the oils are saturated fatty acids and the oils are flowable at a temperature between 0° C. and 4° C.

The saturated fatty acids in the oils produced by the herein described method include, but are not limited to, C12:0 (lauric acid), C14:0 (myristic acid), C15:0 (pentadecylic acid), C16:0 (palmitic acid), C17:0 (margaric acid), and C18:0 (stearic acid). Optionally, the amount of C14:0 (myristic acid) produced by the culturing oil-producing microorganisms in the provided methods is from 8 to 12% of the total saturated fatty acids. Optionally, the amount of C16:0 (palmitic acid) produced by the culturing oil-producing microorganisms in the provided methods is from 14 to 22% of the total saturated fatty acids. Optionally, the amount of C12:0 (lauric acid), C15:0 (pentadecylic acid), C17:0 (margaric acid), and C18:0 (stearic acid) produced by the cultured oil-producing microorganisms in the provided methods is from 0 to 2% of the total saturated fatty acids The provided methods also produce oils having omega-7 fatty acids. The herein provided oils have higher omega-7 fatty acids as compared to a control oils produced by previous fermentation methods. The terms higher, increases, elevates, or elevation refer to increases above a control. For example, control levels are levels prior to, or in the absence of, addition of an agent. Typically, oils produced by microorganisms (i.e., control oils) using other fermentation methods have less than 5% omega-7 fatty acids. As described herein, culturing the oil-producing microorganisms in the fermentation medium in the presence of one or more antifoaming agents under a controlled carbon consumption rate, optionally, produces oils with from 10 to 30% omega-7 fatty acids. Thus, of the total fatty acids in the oils produced by the provided methods 10, 11, 12, 13, 14, 15, 16, 17, 18, 19, 20, 21, 22, 23, 24, 25, 26, 27, 28, 29, or 30% or more of the total fatty acids can be omega-7 fatty acids. The omega-7 fatty acids in the oils include, for example, palmitoleic acid (C16:1(n-7)), cis-vaccenic acid (C18:1(n-7)) or a combination thereof.

The oils produced by the provided methods can also include alpha linolenic acid, arachidonic acid, docosahexanenoic acid, docosapentaenoic acid, eicosapentaenoic acid, gamma-linolenic acid, linoleic acid, linolenic acid, or a combination thereof. Optionally, the oils comprise fatty acids selected from the group consisting of palmitic acid (C16:0), myristic acid (C14:0), palmitoleic acid (C16:1(n-7)), vaccenic acid (C18:1(n-7)), docosapentaenoic acid (C22:5(n-6)), docosahexaenoic acid (C22:6(n-3)), and combinations thereof.

Oil that is produced using the provided methods can be obtained from a variety of microorganisms. The oil can be derived from a population of microorganisms, e.g., oil-producing algae, fungi, bacteria and protists. The microorganisms are optionally selected from the genus *Oblongichytrium, Aurantiochytrium, Thraustochytrium, Schizochytrium*, and *Ulkenia* or any mixture thereof. Optionally, the microorganism is a thraustochytrid of the order Thraustochytriales, more specifically Thraustochytriales of the genus *Thraustochytrium*. Exemplary microorganisms include *Thraustochytriales* as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18), as described in U.S. Pat. No. 8,163,515, which is incorporated by reference herein in its entirety. Thus, optionally, the microorganisms are of the family Thraustochytriaceae. Optionally, the microorganisms are of the genus *Thraustochytrium*. Optionally, the microorganisms are ONC-T18.

Microalgae are acknowledged in the field to represent a diverse group of organisms. For the purpose of this document, the term microalgae is used to describe unicellular microorganisms derived from aquatic and/or terrestrial environments (some cyanobacteria are terrestrial/soil dwelling). Aquatic environments extend from oceanic environments to freshwater lakes and rivers, and also include brackish environments such as estuaries and river mouths. Microalgae can be photosynthetic; optionally, microalgae are heterotrophic. Microalgae can be of eukaryotic nature or of prokaryotic nature. Microalgae can be non-motile or motile.

The term thraustochytrid, as used herein, refers to any member of the order Thraustochytriales, which includes the family Thraustochytriaceae. Strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporuni*), Japoniochytrium (Species: sp., *marinum*), Aplanochytrium (Species: sp., *haliotidis, kerguelensis, profunda, stocchinoi*), Althornia (Species: sp., *crouchii*), or Elina (Species: sp., *marisalba, sinorifica*). Species described within *Ulkenia* are considered to be members of the genus *Thraustochytrium*. Strains described as being within the genus *Thraustochytrium* may share traits in common with and also be described as falling within the genus *Schizochytrium*. For example, in some taxonomic classifications ONC-T18 may be considered within the genus *Thraustochytrium*, while in other classifications it may be described as within the genus *Schizochytrium* because it comprises traits indicative of both genera.

As described, the microorganisms provided herein are cultivated under conditions that produce a compound of interest (e.g., less than 35% saturated fatty acids). The culturing can be carried out for one to several days. Optionally, the method further includes extracting the oils from the microorganisms. The provided methods include or can be used in conjunction with additional steps for culturing microorganisms according to methods known in the art and obtaining the oils therefrom. For example, a Thraustochytrid, e.g., a *Thraustochytrium*, can be cultivated and extracted according to methods described in U.S. Patent Publications 2009/0117194, 2012/0244584, or 2015/0176042, which are herein incorporated by reference in their entireties for each step of the methods or composition used therein.

To isolate oils from microorganisms, the microorganisms are grown in a growth medium (also known as culture medium). Any of a variety of media are suitable for use in culturing the microorganisms described herein. Optionally, the medium supplies various nutritional components, including a carbon source and a nitrogen source, for the microorganism. Medium for Thraustochytrid culture can include any of a variety of carbon sources. Examples of carbon sources include fatty acids (e.g., oleic acid), lipids, glycerols, triglycerols, carbohydrates, polyols, amino sugars, and any kind of biomass or waste stream. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine.

The microorganisms can be cultured in saline or salt-containing medium. The selected culture medium optionally includes NaCl or natural or artificial sea salt and/or artificial seawater. Thraustochytrids can be cultured, for example, in medium having a salt concentration from about 0.5 g/L to about 50.0 g/L, from about 0.5 g/L to about 35 g/L, or from about 18 g/L to about 35 g/L. Optionally, the Thraustochytrids described herein can be grown in low salt conditions (e.g., salt concentrations from about 0.5 g/L to about 20 g/L or from about 0.5 g/L to about 15 g/L).

Alternatively, the culture medium can include non-chloride-containing sodium salts as a source of sodium, with or without NaCl. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

Media for microbial cultures can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

The resulting biomass can be pasteurized to inactivate undesirable substances present in the biomass. For example, the biomass can be pasteurized to inactivate compound degrading substances, such as degradative enzymes. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

The biomass can be harvested according to a variety of methods, including those currently known to one skilled in the art. For example, the biomass can be collected from the fermentation medium using, for example, centrifugation (e.g., with a solid-ejecting centrifuge) and/or filtration (e.g., cross-flow filtration). Optionally, the harvesting step includes use of a precipitation agent for the accelerated collection of cellular biomass (e.g., sodium phosphate or calcium chloride).

The biomass is optionally washed with water. The biomass can be concentrated up to about 20% solids. For example, the biomass can be concentrated from about 1% to about 20% solids, from about 5% to about 20%, from about 7.5% to about 15% solids, or to any percentage within the recited ranges.

Optionally, the oils can be further processed, e.g., by winterization. Prior to winterization, the oils or polyunsaturated fatty acids are obtained or extracted from the biomass or microorganisms using one or more of a variety of methods, including those currently known to one of skill in the art. For example, methods of isolating oils or polyunsaturated fatty acids are described in U.S. Pat. No. 8,163,515, which is incorporated by reference herein in its entirety. Alternatively, the oils or polyunsaturated fatty acids are isolated as described in U.S. Publication No. 2015/0176042, which is incorporated by reference herein in its entirety. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

Oils, lipids or derivatives thereof (e.g., polyunsaturated fatty acids (PUFAs) and other lipids) can be utilized in any of a variety of applications exploiting their biological, nutritional, or chemical properties. Thus, the oils, lipids or derivatives thereof can be used to produce biofuel. Optionally, the oils, lipids or derivatives thereof, are used in pharmaceuticals, nutraceuticals, food supplements, animal feed additives, cosmetics, and the like.

Optionally, the liquid fractions of oils or the solid fractions of oils produced according to the methods described herein can be incorporated into a final product (e.g., a food or feed supplement, an infant formula, a pharmaceutical, a fuel, and the like). Optionally, the solid fractions are incorporated into animal feed. Optionally, the liquid fractions are incorporated into a food supplement, e.g., a nutritional or dietary supplement such as a vitamin. Suitable food or feed supplements into which the oils or lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like.

Optionally, one or more of the oils or compounds therein (e.g., PUFAs) can be incorporated into a nutraceutical or pharmaceutical product. Examples of such nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oils or oil portions thereof produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

A thraustochytrid strain named T18 was used in all examples. Similar to other thraustochytrids, this strain produces lipids that contains several major fatty acids, including C14:0 myristic acid, C16:0 palmitic acid, C16:1 (n-7) palmitoleic acid, C18:1 (n-9) vaccenic acid, C22:5 (n-6)

docosapentaenoic acid (DPA) and C22:6 (n-3) docosahexaenoic acid (DHA). As described herein, depending on fermentation conditions applied, the level of synthesis of each major fatty acids may be altered, and consequently the relative content of these major fatty acids within the entire oil can be varied. The different process conditions lead lipid synthesis toward more desirable fatty acid profiles, namely higher DHA and higher MUFA and reduced SFA.

Example 1. Microbial Fermentations without Applying Controlled Carbon Consumption Rate This example illustrates typical fatty acid profiles attainable by microbial fermentations with unrestricted carbon consumption rate. Fermentation was carried out in a 500 L fermentor with working volume between 150 L and 350 L, with the increase in volume due to the feeding of glucose syrup during the fermentation. Initial fermentation medium contained (per liter): glucose 60 g, soy peptone 2 g; sodium chloride 1.65 g; magnesium sulfate heptahydrate 4 g; potassium phosphate monobasic 2.2 g; potassium phosphate dibasic 2.4 g; ammonium sulfate 20 g; calcium chloride dihydrate 0.1 g; iron chloride 0.003 g; copper sulfate pentahydrate 0.003 g; sodium molybdate dehydrate 0.0015 g; zinc sulfate heptahydrate 0.003 g; cobalt chloride hexahydrate 0.0015 g; manganese chloride tetrahydrate 0.0015 g; nickel sulfate hexahydrate 0.0015 g; vitamin B12 0.00003 g; biotin 0.00003 g; thiamin hydrochloride 0.006 g. A silicon based antifoam was used sparingly to suppress foam formation when necessary, and less than 0.3 g/L of this antifoam was used throughout the entire fermentation. Agitation, aeration and backpressure of the fermentor were controlled such that the culture had unrestricted carbon consumption rate that was up to 10 g/L-h (FIG. 1). Additional carbon in the form of glucose syrup was fed to the fermentor throughout the culturing or fermentation such that there was always glucose available in the media for the culture to consume.

Figure 2:
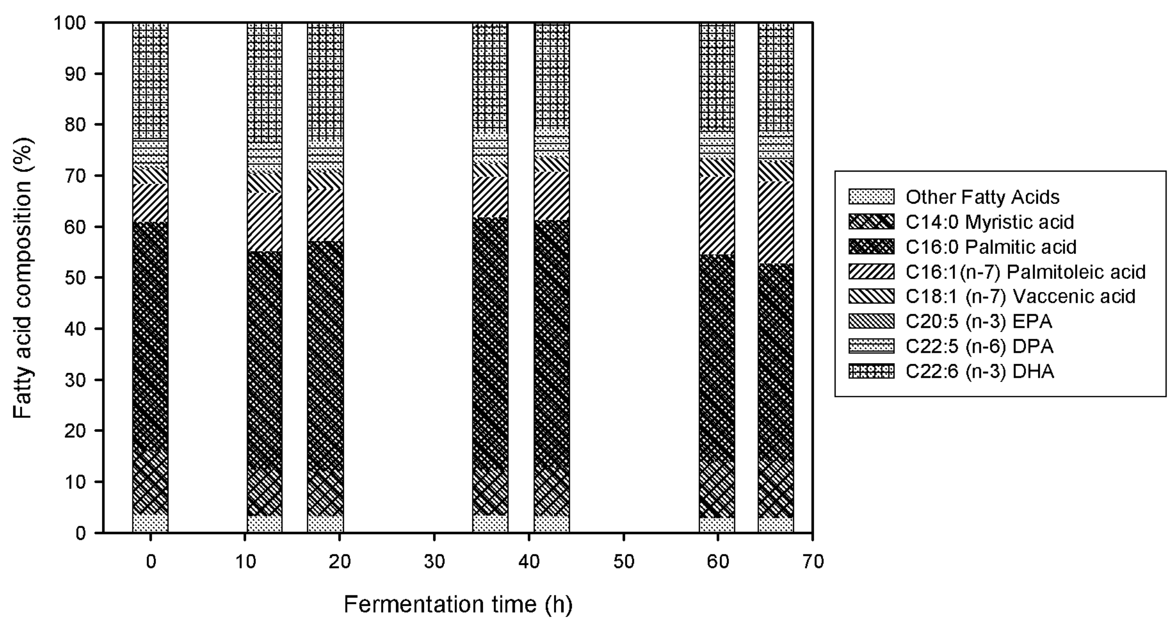
FIG. 2 is a graph showing the time profile of fatty acid compositions during microbial oil fermentation with unrestricted carbon consumption rate.

As demonstrated by the time profile of fatty acid composition (FIG. 2), DHA content was relatively low, ranging between 20% and 23% of total fatty acids, throughout the fermentation. With the unrestricted carbon consumption rate, the final attained oil contained only 21% DHA, much less than 35-40% DHA that is required in a commercial DHA-rich microbial oil.

The reproducibility of such a final profile with relatively low DHA content was demonstrated by two batches of 500 L fermentations shown in Table 1. Although total MUFA (C16:1 n-7 palmitoleic acid and C18:1 n-7 vaccenic acid) in these fatty acid profiles were between 15 and 20% and can be considered significant, the relatively low content of DHA would render this overall profile undesirable as a commercial DHA-rich algal oil.

TABLE 1

Fatty acid profile of low DHA microbial fermentation.

| Major fatty acids (%)[1] | Final fatty acid profile of low DHA microbial fermentation | |
|---|---|---|
| | Batch #1 | Batch #2 |
| Other fatty acids | 2.97 | 3.17 |
| C14:0 Myristic acid | 11.18 | 12.53 |
| C16:0 Palmitic acid | 38.70 | 41.96 |
| C16:1 (n-7) Palmitoleic acid | 16.15 | 13.28 |
| C18:1 (n-7) Vaccenic acid | 3.73 | 3.42 |
| C20:5 (n-3) EPA | 0.39 | 0.37 |
| C22:5 (n-6) DPA | 5.54 | 5.05 |
| C22:6 (n-3) DHA | 21.33 | 20.21 |

Example 2. High-DHA Fermentation with Controlled Carbon Consumption Rate

Figure 3:
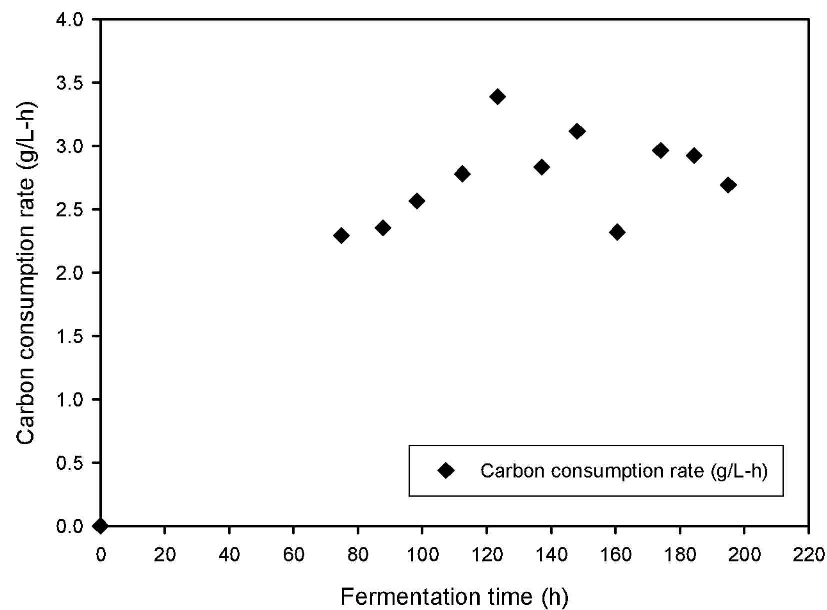
FIG. 3 is a graph showing controlled carbon consumption rate during a high-DHA microbial fermentation.

This example illustrates high-DHA fatty acid profiles obtained by microbial fermentations of the same strain using specific carbon consumption rate control. Fermentation was carried out in a 500 L fermentor. Initial fermentation medium contained the same nutrient formulation as example 1, except that soy peptone and sodium chloride concentration were increased to 10 g/L and 9 g/L, respectively. A silicon based antifoam was used sparingly to suppress foam formation when necessary, and less than 0.3 g/L of this antifoam was used throughout the entire fermentation. Agitation, aeration and backpressure of the fermentor were controlled such that the culture could only reach restricted carbon consumption rate throughout the run, as demonstrated in FIG. 3. Additional carbon source in the form of glucose syrup was fed to the fermentor throughout the fermentation such that there was always glucose available in the media for the culture to consume.

Figure 4:
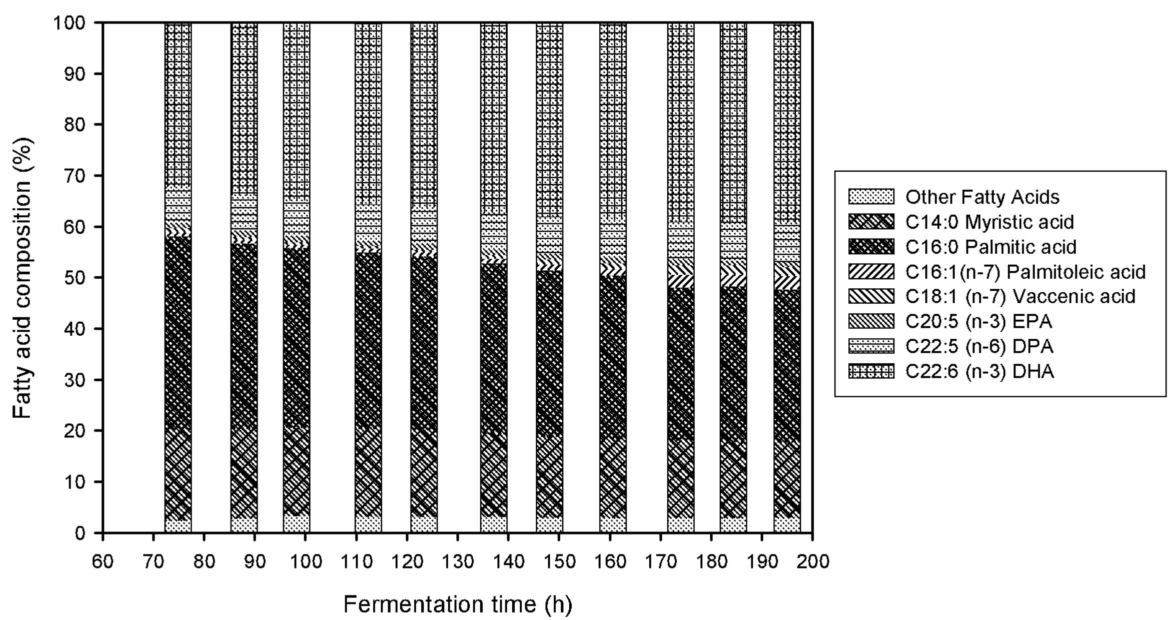
FIG. 4 is a graph showing the time profile of fatty acid compositions during microbial oil fermentation with controlled carbon consumption rate.
Figure 5:
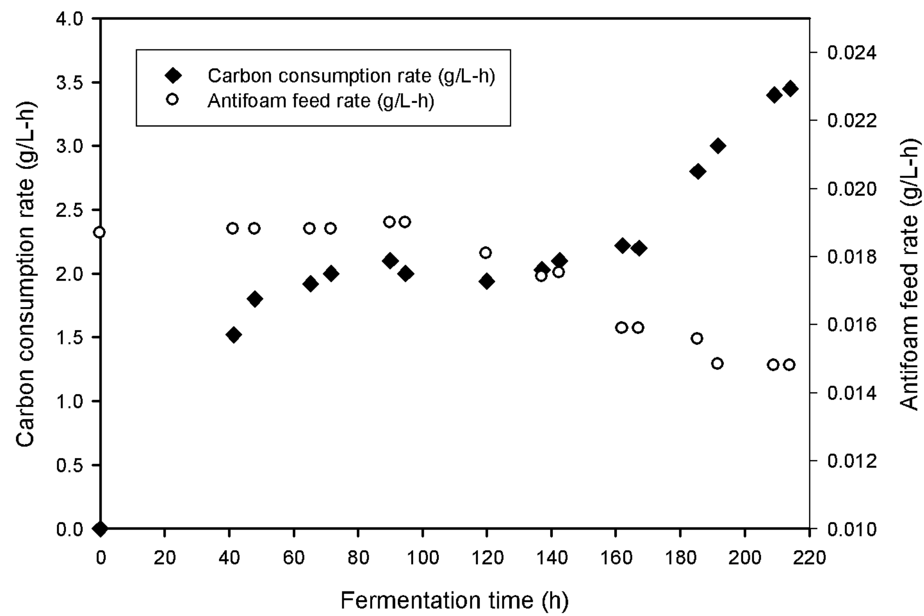
FIG. 5 is a graph showing the controlled carbon consumption rate and continuous antifoam addition during a high-DHA/high-MUFA microbial fermentation.

As demonstrated by the time profile of fatty acid composition (FIG. 4), by applying controlled carbon consumption rate, DHA content could be controlled within a relatively high range, between 33% and 40%, throughout the fermentation. The final fatty acid profile contained 39.2% DHA, which met the commercial requirement for a DHA-rich lipids (DHA>35%). However, this fermentation process produced much less MUFA compared to the process with unrestricted carbon consumption rate shown in Example 1. With saturated fatty acids (SFA) being nearly 50% of the entire profile, the resulting lipid had a relatively high pour point of 24° C., rendering the oil non-flowable at room temperature.

The reproducibility of such a final profile with relatively high DHA and low MUFA content was demonstrated by three batches of fermentations ranging from lab scale (7 L, batch #1), small pilot scale (30 L, batch #2) and pilot scale (500 L, batch #3), as shown in Table 2. The high DHA content meets commercial requirement for DHA-rich oil. However, this oil would require heating and elevated temperature during processing, which may introduce added processing cost and compromise long-term stability of the oil.

TABLE 2

Fatty acid profile of high DHA/low MUFA microbial fermentation.

| Major fatty acids (%)[1] | Final fatty acid profile of high DHA/low MUFA microbial fermentation | | |
|---|---|---|---|
| | Batch #1 | Batch #2 | Batch #3 |
| Other fatty acids | 3.87 | 3.76 | 3.40 |
| C14:0 Myristic acid | 13.80 | 12.37 | 13.44 |
| C16:0 Palmitic acid | 28.44 | 30.97 | 30.11 |

TABLE 2-continued

Fatty acid profile of high DHA/low MUFA microbial fermentation.

| Major fatty acids (%)[1] | Final fatty acid profile of high DHA/low MUFA microbial fermentation | | |
|---|---|---|---|
| | Batch #1 | Batch #2 | Batch #3 |
| C16:1 (n-7) Palmitoleic acid | 1.95 | 0.60 | 1.78 |
| C18:1 (n-7) Vaccenic acid | 1.76 | 0.70 | 1.35 |
| C20:5 (n-3) EPA | 0.89 | 1.10 | 0.78 |
| C22:5 (n-6) DPA | 6.54 | 7.92 | 7.38 |
| C22:6 (n-3) DHA | 42.77 | 42.58 | 41.77 |

Example 3. High-DHA Fermentation with Controlled Carbon Consumption Rate and Continuous Antifoam Addition This example illustrates high-DHA fatty acid profiles obtained by microbial fermentations of the same strain using a combination of controlled carbon consumption rate and continuous antifoam addition. Fermentation was carried out in a 500 L fermentor. Initial fermentation medium contained the same nutrient formulation as example 1, except that sodium chloride concentration was increased to 9 g/L. A vegetable oil based antifoaming agent was added continuously throughout the fermentation at a rate between 0.014 g/L-h and 0.020 g/L-h. Agitation, aeration and backpressure of the fermentor were controlled such that the culture could only reach restricted carbon consumption rate throughout the fermentation, as demonstrated in FIG. 4. Additional carbon in the form of glucose syrup was fed to the fermentor throughout the fermentation such that there was always glucose available in the medium for the culture to consume.

Figure 6:
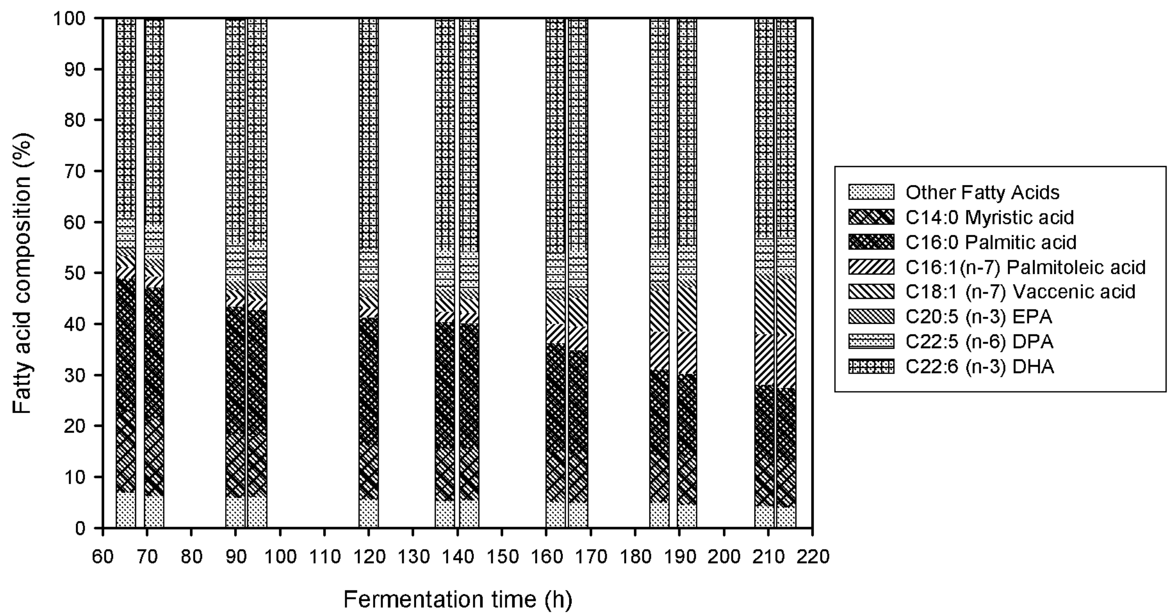
FIG. 6 is a graph showing the time profile of fatty acid compositions during microbial oil fermentation with controlled carbon consumption rate and continuous antifoam addition.

As demonstrated by the time profile of fatty acid composition (FIG. 6), by applying controlled carbon consumption rate in combination with continuous antifoam addition, not only could DHA content be controlled around 40%, MUFA synthesis during later stage of the fermentation was also significant and it reached over 20% of total lipid at the end. With saturated fatty acids (SFA) being reduced to below 30% of the entire profile, the resulting oil had much better cold flow property, which can be reflected by the pour point of −9° C.

The reproducibility of such a final profile with relatively high DHA and high MUFA content was demonstrated by three batches of fermentations ranging from lab scale (7 L, batch #1) to pilot scale (500 L, batch #2 and #3), as shown in Table 3. The high DHA content meets commercial requirement for DHA-rich algal oil. Meanwhile, this oil now contains significant content of omega-7 MUFA and much lower content of SFA. Such changes in the fatty acid profile make the oil much easier to handle during processing, and provided added nutritional value.

TABLE 3

Fatty acid profile of high DHA/high MUFA microbial fermentation.

| Major fatty acids (%)[1] | Final fatty acid profile of high DHA/high MUFA microbial fermentation | | |
|---|---|---|---|
| | Batch #1 | Batch #2 | Batch #3 |
| Other fatty acids | 5.17 | 5.49 | 5.24 |
| C14:0 Myristic acid | 7.94 | 11.03 | 9.47 |
| C16:0 Palmitic acid | 17.09 | 18.23 | 14.40 |

TABLE 3-continued

Fatty acid profile of high DHA/high MUFA microbial fermentation.

| Major fatty acids (%)[1] | Final fatty acid profile of high DHA/high MUFA microbial fermentation | | |
|---|---|---|---|
| | Batch #1 | Batch #2 | Batch #3 |
| C16:1 (n-7) Palmitoleic acid | 7.36 | 7.56 | 10.28 |
| C18:1 (n-7) Vaccenic acid | 10.33 | 6.34 | 10.98 |
| C20:5 (n-3) EPA | 1.35 | 1.47 | 1.17 |
| C22:5 (n-6) DPA | 7.32 | 7.10 | 6.40 |
| C22:6 (n-3) DHA | 43.45 | 42.79 | 42.06 |

Figure 7:
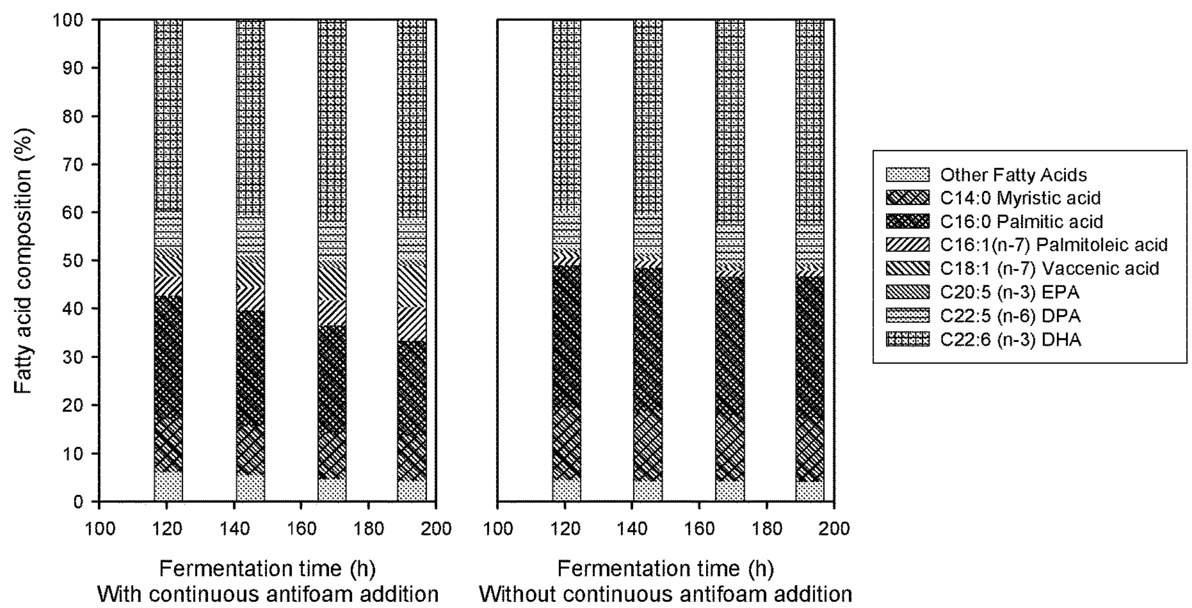
FIG. 7 is a graph showing the effect of continuous antifoam addition to the fatty acid profile during microbial fermentation.

Example 4. Effect of Continuous Antifoam Addition to High-DHA Fatty Acid Profiles This example illustrates the effect of continuous antifoam addition by running two fermentations in parallel, of which one received continuous antifoam addition and the other one did not. All other fermentation factors were the same, including inoculum from the same seed flask, identical initial medium, fed medium, working volume, temperature, pH, aeration, and range of controlled carbon consumption rate. As shown in FIG. 7, the continuous antifoam addition enabled the significant synthesis of MUFA during the later stage of the fermentation, resulting in an oil that was physically and nutritionally more favorable when compared to high-DHA/low MUFA lipids.

Figure 8:
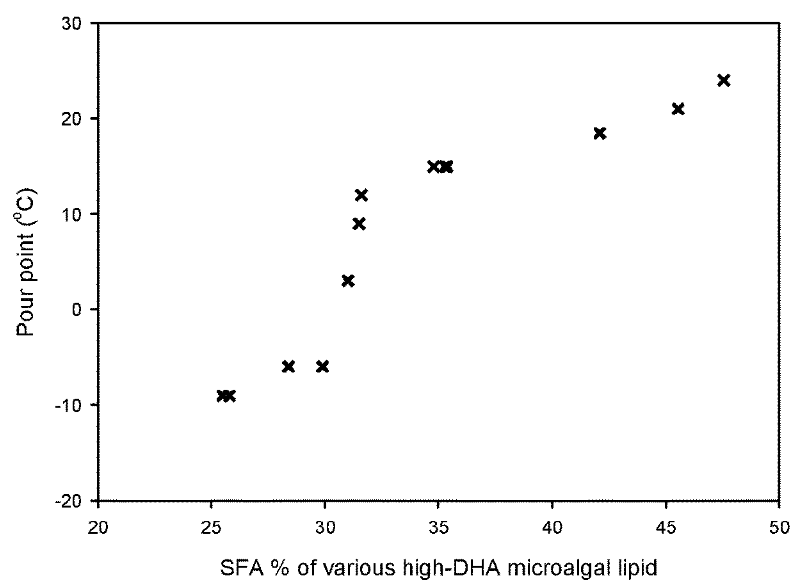
FIG. 8 is a graph showing the correlation between SFA content in the high-DHA microbial oils and their pour point.

Example 5. Improvement on Cold Flow Properties by Varying Lipid Fatty Acid Profiles This example illustrates the correlation between SFA content in the high-DHA microbial lipids and their cold flow property, which is reflected by their pour points. The pour points of thirteen batches of high-DHA (>37%) microbial lipids were plotted against the SFA content of each lipid. As seen in FIG. 8, lipids produced without continuous antifoam addition have higher than 40% SFA and their pour points are at or above room temperature. Oil produced with continuous antifoam addition and controlled carbon consumption rate has lower than 35% SFA. A decrease in pour points can be observed when the SFA % are reduced to 35% and below. When the SFA content is reduced, those oils exhibited very little crystallization behavior, and consequently they remained in an liquid state even, in some cases, at sub-zero temperatures.

What is claimed is:

1. A method of producing a microbial oil comprising fatty acids, wherein the method comprises:

culturing oil-producing Thraustochytrid microorganisms in a fermentation medium in the presence of one or more antifoaming agents continuously added to the fermentation medium under a controlled carbon consumption rate of between 1.5 and 4.5 g/L per hour, wherein the culturing produces an oil comprising:

(a) saturated fatty acids, wherein 20% to 35% of the fatty acids are saturated fatty acids;

(b) omega-7 fatty acids, wherein 10-30% of the fatty acids are omega-7 fatty acids comprising C16:1 (n-7) palmitoleic acid and C18:1 (n-7) cis-vaccenic acid, and (c) docosahexaenoic acid (DHA), wherein greater than 35% of the fatty acids are DHA.

2. The method of claim 1, wherein the antifoaming agent is a mineral oil based antifoaming agent, vegetable oil based antifoaming agent, silicon based antifoaming agent, oil/water emulsion based antifoaming agent, polyethylene glycol (PEG) based antifoaming agent, or a polypropylene glycol based antifoaming agent.

3. The method of claim 1, wherein the antifoaming agent is a vegetable oil based antifoaming agent and wherein the vegetable oil based antifoaming agent is soybean oil or rapseed oil.

4. The method of claim 1, wherein the antifoaming agent is a silicon based antifoaming agent and wherein the silicon based antifoaming agent is poly dimethyl siloxane.

5. The method of claim 1, wherein the one or more antifoaming agents are added to the fermentation medium at a rate of 0.0075 to 0.05 g/L per hour throughout the culturing.

6. The method of claim 1, wherein the carbon consumption rate is controlled by aeration, agitation, vessel backpressure or a combination thereof.

7. The method of claim 1, wherein the carbon consumption rate is controlled by continuous addition of one or more carbon source(s) throughout the culturing.

8. The method of claim 1, wherein the melting point of the oil is from 20 to 33° C.

9. The method of claim 1, wherein the cloud point of the oil is from 5 to 20° C.

10. The method of claim 1, wherein the pour point of the oil is from −10 to 15° C.

11. The method of claim 1, wherein culturing is carried out for one to several days.

12. The method of claim 1, wherein the saturated fatty acids comprise myristic acid and palmitic acid.

13. The method of claim 10, wherein 8-12% of the saturated fatty acids are myristic acid.

14. The method of claim 10, wherein 14-22% of the saturated fatty acids are palmitic acid.

15. The method of claim 1, wherein less than 2% of the saturated fatty acids comprise one or more of lauric acid, pentadecyclic acid, margaric acid and stearic acid.

16. The method of claim 1, wherein the oil comprises about 7 or about 10% of the C16:1 (n-7) palmitoleic acid.

17. The method of claim 1, wherein the oil comprises about 6 or about 10% of the C18:1 (n-7) cis-vaccenic acid.

18. The method of claim 1, wherein the oil comprises docosapentanoic acid (DPA).

19. The method of claim 1, wherein 25% to 30% of the fatty acids in the oil are saturated fatty acids and wherein the oil is flowable at a temperature between −9° C. and 9° C.

20. The method of claim 1, wherein the microorganisms are of the family Thraustochytriaceae.

21. The method of claim 1, wherein the microorganisms are of the genus *Thraustochytrium.*

22. The method of claim 1, wherein the microorganisms have ATCC Accession No. PTA-6245.

23. The method of claim 1, further comprising extracting the oil from the microorganisms.

* * * * *